United States Patent
Zhang et al.

(10) Patent No.: US 12,228,528 B2
(45) Date of Patent: Feb. 18, 2025

(54) FOOD PRODUCT MONITORING SOLUTION

(71) Applicant: MEKITEC OY, Oulu (FI)

(72) Inventors: Peng Zhang, Xi'an (CN); Yuanhui Wei, Xi'an (CN); Mikko Nuutinen, Espoo (FI); Antti Sivula, Helsinki (FI)

(73) Assignee: MEKITEC OY, Oulu (FI)

( * ) Notice: Subject to any disclaimer, the term of this patent is extended or adjusted under 35 U.S.C. 154(b) by 321 days.

(21) Appl. No.: 17/785,826

(22) PCT Filed: Dec. 16, 2019

(86) PCT No.: PCT/CN2019/125722
§ 371 (c)(1),
(2) Date: Jun. 15, 2022

(87) PCT Pub. No.: WO2021/119946
PCT Pub. Date: Jun. 24, 2021

(65) Prior Publication Data
US 2023/0058730 A1     Feb. 23, 2023

(51) Int. Cl.
*G01N 23/083* (2018.01)
*G01N 23/04* (2018.01)
(Continued)

(52) U.S. Cl.
CPC ........... *G01N 23/083* (2013.01); *G01N 23/04* (2013.01); *G01N 33/02* (2013.01); *G06T 7/0004* (2013.01);
(Continued)

(58) Field of Classification Search
CPC .................. G06V 10/82; G06V 10/70; G06V 10/778–10/7796; G06V 10/454;
(Continued)

(56) References Cited

U.S. PATENT DOCUMENTS

| | | |
|---|---|---|
| 6,546,071 B2 | 4/2003 | Graves |
| 7,450,686 B2 | 11/2008 | Ainsworth et al. |

(Continued)

FOREIGN PATENT DOCUMENTS

| | | |
|---|---|---|
| CN | 108254397 | 7/2018 |
| CN | 108364017 | 8/2018 |

(Continued)

OTHER PUBLICATIONS

International Search Report dated Sep. 18, 2020, for PCT/CN2019/125722, 5 pp.

(Continued)

*Primary Examiner* — Mia M Thomas
(74) *Attorney, Agent, or Firm* — NIXON & VANDERHYE (57) ABSTRACT

Disclosed is a method for inspecting a food product, the method includes: receiving image data representing the food product captured with an X-ray imaging unit; performing a texture analysis to image data for generating a first set of detections; performing a pattern analysis to at least part of the image data, the pattern analysis performed with a machine-learning component trained to identify objects with predefined pattern, for generating a second set of detections; generating an indication of an outcome of an inspection of the food product in accordance with a combination of the generated first set of detections and the second set of detections. Also disclosed is an apparatus and a computer program product.

14 Claims, 4 Drawing Sheets

(51) Int. Cl.
  *G01N 33/02* (2006.01)
  *G06T 7/00* (2017.01)
  *G06T 7/40* (2017.01)
  *G06V 10/44* (2022.01)
  *G06V 10/54* (2022.01)
  *G06V 10/82* (2022.01)
  *G06V 20/00* (2022.01)
  *G06V 20/68* (2022.01)

(52) U.S. Cl.
  CPC .............. *G06T 7/40* (2013.01); *G06V 10/454* (2022.01); *G06V 10/54* (2022.01); *G06V 10/82* (2022.01); *G06V 20/00* (2022.01); *G01N 2223/618* (2013.01); *G06T 2207/10116* (2013.01); *G06T 2207/20081* (2013.01); *G06T 2207/20084* (2013.01); *G06T 2207/30128* (2013.01); *G06V 20/68* (2022.01)

(58) Field of Classification Search
  CPC .................... G06V 20/68; G06V 10/54; G06T 2207/20084; G06T 2207/30128; G06T 2207/10116; G06T 7/40–7/49; G01N 33/02–33/146; G01N 2223/618; G01N 23/083–23/185
  See application file for complete search history.

(56) References Cited

U.S. PATENT DOCUMENTS

| | | | | |
|---|---|---|---|---|
| 10,006,873 | B1* | 6/2018 | Davis, III | G01N 33/12 |
| 11,475,404 | B2* | 10/2022 | Adato | G06Q 10/0875 |
| 11,769,244 | B2* | 9/2023 | McDonnell | G06N 20/00 382/110 |
| 11,922,673 | B2* | 3/2024 | Liu | G06T 7/11 |
| 2002/0012419 | A1* | 1/2002 | Graves | G01N 33/12 378/53 |
| 2010/0150308 | A1* | 6/2010 | Tsuno | G01G 11/00 378/57 |
| 2017/0178312 | A1 | 6/2017 | Li et al. | |
| 2019/0318471 | A1* | 10/2019 | Chen | G01N 21/8851 |
| 2020/0134371 | A1* | 4/2020 | Charraud | G06V 10/82 |
| 2020/0386690 | A1* | 12/2020 | Furihata | G06T 7/0008 |
| 2022/0207684 | A1* | 6/2022 | Sugino | G06T 7/001 |
| 2023/0148640 | A1* | 5/2023 | Takai | G01N 21/85 426/46 |

FOREIGN PATENT DOCUMENTS

| | | | |
|---|---|---|---|
| CN | 109791111 | 5/2019 | |
| CN | 109886926 | 6/2019 | |
| CN | 109948412 | 6/2019 | |
| EP | 2081012 A1 * | 7/2009 | ......... G01N 21/3563 |
| EP | 2081013 A1 * | 7/2009 | ......... G01N 21/3563 |
| WO | 2019/235022 | 12/2019 | |

OTHER PUBLICATIONS

Written Opinion of the International Searching Authority dated Sep. 18, 2020, for PCT/CN2019/125722, 5 pp.

Qiang Wang et al., "Recognition of Dumplings with Foreign Body Based on X-Ray and Convolutional Neural Network", Food Science, vol. 40, No. 16, 2019, pp. 314-320 (English abstract provided).

Supplementary EP Search Report issued in EP Patent Application No. 19 95 6235 dated Sep. 14, 2023.

Amza et al., "Flexible Neural Network Classifier for the Automated Detection of Bones in Chicken Breast Meat," Proc. International Conference on Engineering Applications of Neural Networks Jul. 17-19, 2000, Retrieved from the Internet: URL:https://www.researchgate.net/publication/2374721_Flexible_Neural_Network_Classifier_For_The_Automated_Detection_Of_Bones_In_Chicken_Breast_Meat, retrieved on Sep. 14, 2023, 8 pages.

* cited by examiner

FOOD PRODUCT MONITORING SOLUTION

This application is the U.S. national phase of International Application No. PCT/CN2019/125722 filed Dec. 16, 2019, which designated the U.S., the entire contents of which are hereby incorporated by reference.

TECHNICAL FIELD

The invention concerns in general the technical field of food inspection. More particularly, the invention concerns food inspection system based on image analysis.

BACKGROUND

As is commonly known food production is more and more automated nowadays. Food production lines produce food products being packed in a predetermined manner and conveyed to a transport station for delivering the food products to grocery stores and similar.

A quality of the food products is always a core issue in the food production. This refers to an idea that the food product itself complies with quality standards, but also that the product as a whole contains only those elements belonging to the food product in question. For example, a food product may be a so-called semi-finished product whose finalization is performed by a user. The food product may e.g. comprise the food itself, but some further elements like spices packed e.g. in plastics which are to be included in the food product after heating. Hence, it may be essential to confirm that the food product includes all the elements belonging to the product when exported from the factory. Equally important it is to guarantee that the food product does not contain foreign matter not belonging to the food product itself. Such foreign matter may have been ended up to the food product from the food production line or together with the raw material used for the food product.

At least some of the above mentioned issues are addressed by taking the food products, or the raw material, at some point of a process through a food inspection device. Depending on a type of the food inspection device predetermined characteristics of the food product are determined and based on them an analysis is performed in order to determine if the food product complies with quality standards set for the product.

Some food inspection devices in use are based on the food product imaging system including hardware and software. The imaging may be based on using X-rays for capturing the image of the food product. The analysis performed to the X-ray image of the food product is achieved by identifying the X-ray intensity differences in objects represented in the X-ray image. On the basis of the X-ray intensity differences analysis it is possible, to some extent, detect if the food product complies with the quality standard. An example of such a food inspection device is disclosed in a document U.S. Pat. No. 7,450,686B2.

By discriminating the basis of X-ray intensity differences between the objects in the image, a challenge with the food inspection devices based on X-rays and the analysis is that they have limited accuracy as well as in a situation that the objects are overlapping in the food product when the image is captured. Hence, a reliability of the inspection device in question is somewhat limited. In order to mitigate at least in part the drawbacks of the existing solutions, it is necessary to introduce more sophisticated solutions for improving the reliability at least in part.

SUMMARY

The following presents a simplified summary in order to provide basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

An object of the invention is to present a method, an apparatus and a computer program product for inspecting a food product.

The objects of the invention are reached by a method, an apparatus and a computer program product as defined by the respective independent claims.

According to a first aspect, a method for inspecting a food product is provided, the method comprises: receiving image data representing the food product captured with an X-ray imaging unit; performing a texture analysis to image data for generating a first set of detections; performing a pattern analysis to at least part of the image data, the pattern analysis performed with a machine-learning component trained to identify objects with predefined pattern, for generating a second set of detections; generating an indication of an outcome of an inspection of the food product in accordance with a combination of the generated first set of detections and the second set of detections.

The texture analysis may comprise a generation of a sub-set of the first set of detections, the sub-set comprising detections having a likelihood within a predetermined range. The at least part of the image data to which the pattern analysis is performed may correspond to the sub-set of the first set of detections. For example, an outcome of the pattern analysis performed to the sub-set of the first set of detections may be one of: the detection performed with the texture analysis is correct, the detection performed with the texture analysis is incorrect.

Moreover, a generation of the indication in accordance with the generated first set of detections and the second set of detections may be arranged by detecting with the texture analysis objects having a size within a first range and detecting with the pattern analysis objects having a size within a second range being at least in part smaller than the first range.

For example, the machine-learning component may be trained with object data derivable from a process by means of which the food product is manufactured.

According to a second aspect, an apparatus for inspecting a food product is provided, the apparatus comprising: an X-ray imaging unit for generating image data representing the food product; a control unit arranged to: receive the image data representing the food product captured with an X-ray imaging unit; perform a texture analysis to the image data for generating a first set of detections; perform a pattern analysis to at least part of the image data, the pattern analysis performed with a machine-learning component trained to identify objects with predefined pattern, for generating a second set of detections; generate an indication of an outcome of an inspection of the food product in accordance with a combination of the generated first set of detections and the second set of detections.

The control unit of the apparatus may be arranged to, in the texture analysis, generate a sub-set of the first set of detections, the sub-set comprising detections having a likelihood within a predetermined range.

The control unit of the apparatus may be arranged to perform the pattern analysis to the at least part of the image data corresponding to the sub-set of the first set of detections. For example, the control unit of the apparatus may be arranged to generate, as an outcome of the pattern analysis performed to the sub-set of the first set of detections, is one of: the detection performed with the texture analysis is correct, the detection performed with the texture analysis is incorrect.

Moreover, the control unit of the apparatus may be arranged to perform a generation of the indication in accordance with the generated first set of detections and the second set of detections by detecting with the texture analysis objects having a size within a first range and detecting with the pattern analysis objects having a size within a second range being at least in part smaller than the first range.

For example, the machine-learning component of the control unit may be arranged to be trained with object data derivable from a process by means of which the food product is manufactured.

According to a third aspect, a computer program product for inspecting a food product is provided which computer program product, when executed by at least one processor, cause an apparatus to perform the method according to the first aspect as described in the foregoing description.

The expression "a number of" refers herein to any positive integer starting from one, e.g. to one, two, or three.

The expression "a plurality of" refers herein to any positive integer starting from two, e.g. to two, three, or four.

Various exemplifying and non-limiting embodiments of the invention both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of unrecited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

The embodiments of the invention are illustrated by way of example, and not by way of limitation, in the figures of the accompanying drawings.

DESCRIPTION OF THE EXEMPLIFYING EMBODIMENTS

The specific examples provided in the description given below should not be construed as limiting the scope and/or the applicability of the appended claims. Lists and groups of examples provided in the description given below are not exhaustive unless otherwise explicitly stated.

Figure 1:
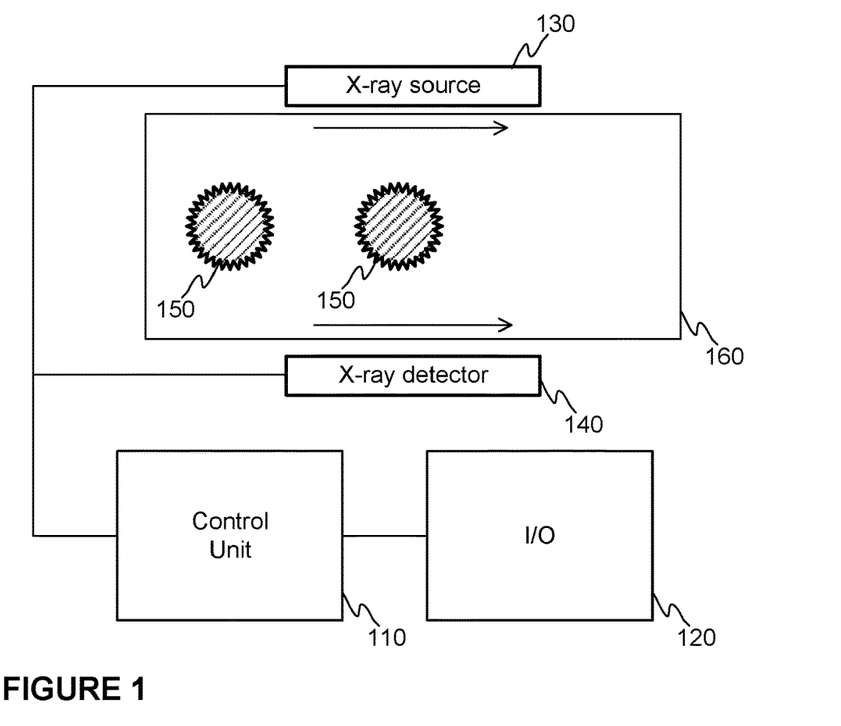
FIG. 1 illustrates schematically a food inspection device according to an embodiment of the invention.

FIG. 1 illustrates schematically a food inspection device according to an example embodiment as a block diagram. The food inspection with the illustrated device is based on utilization of X-rays for scanning objects input to the inspection. The food inspection device according to various embodiments may comprise a control unit 110 arranged to implement control functions for driving the food inspection device. One or more I/O devices 120 may be coupled to the control unit 110. Some non-limiting examples of the I/O devices 120 may be display device(s), keyboard(s), button (s), touch screen(s), loudspeaker(s), microphone(s), light source(s) and so on. Furthermore, the food inspection device may comprise an X-ray imaging unit consisting of X-ray source 130 and X-ray detector 140. The X-ray source 130 is arranged to generate X-rays conveyed towards food product 150 under inspection. The X-ray source 130 may e.g. comprise X-ray tube and collimator as well as further elements. The X-ray detector, in turn, 140 receives the X-rays at least part of which travels through the food product 150 under inspection. The X-ray detector 140 comprises sensors, such as solid-state sensors, for generating a digital image on the object under inspection. However, the term X-ray detector 140 shall be understood in a broad manner and any other type of detector, such as X-ray film, may be used. In any case, at some point the image of the food product is advantageously in a digital form. The control unit 110 may be arranged to generate control signals with respect to the X-ray source 130 and the X-ray detector 140 for example for initiating a generation of X-rays and reading out image data from the X-ray detector 140. Still further, in some embodiments the food inspection device may comprise a conveyor device 160 by means of which the food products may be input and output for inspection. A non-limiting example of the conveyor device 160 may be a conveyor belt. The control unit 110 may also be arranged to control the operation of the conveyor device 160, such as moving it and stopping it e.g. in-sync with the operation of the X-ray source 130 and the X-ray detector 140. The food inspection device may comprise further elements and entities, such as sensors for detecting a position of the food product, for enabling the operation of the food inspection device.

Figure 2:
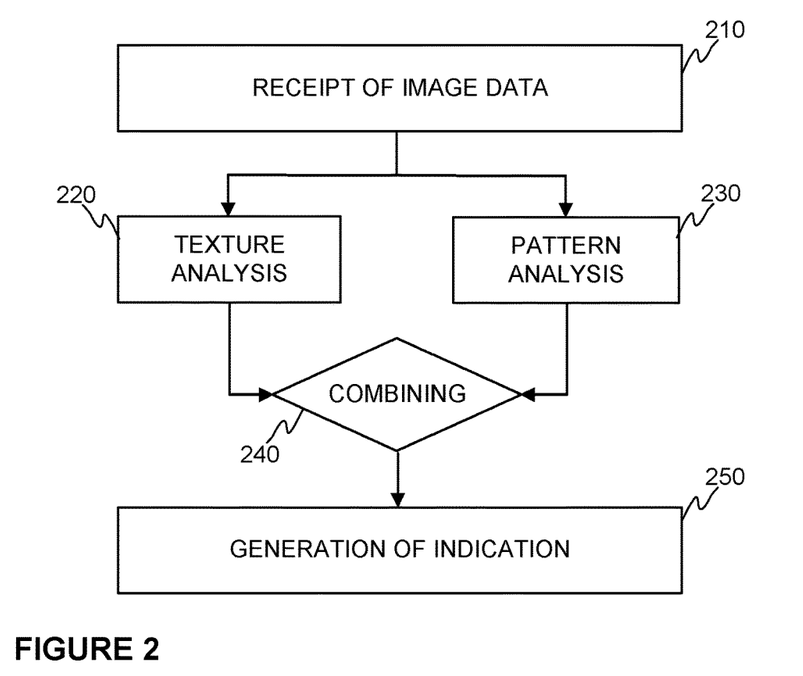
FIG. 2 illustrates schematically a method according to an embodiment of the invention.

Next, some further aspects are now discussed by referring to FIG. 2 illustrating schematically a method according to various embodiments. For example, the control unit 110 may be arranged to control the X-ray imaging unit to perform image capturing process e.g. in response to a detection that a food product resides in an applicable position for imaging within the food inspection device. In response to the capture of the image the food inspection device, and especially the control unit 110, may receive 210 image data representing an image of the food product captured with an X-ray imaging unit. The received image data is in a form of digital data to which analysis operations may be performed.

In response to the receipt of image data the control unit 110 may be arranged to perform a texture analysis 220 to the image data received from the X-ray imaging unit. The texture analysis may be performed due to a fact that X-rays may penetrate an object in accordance with characteristics of the object in question thus generating a texture in the image representing the objects. A non-limiting example source of different textures is a variety of intensity differences in the object under imaging and, hence, in some example embodiments the texture analysis may refer to intensity differences analysis. In other words, the characteristics of the object attenuate the X-ray radiation in a varied way, and as a result the X-ray detector receives a varied amount of radiation. The variation is detectable from the image as a variation of textures, such as contrast, in the image. Hence, the texture, such as the contrast, may be considered to have a relationship to the material of the food product 150, and specifically to the characteristics of the food product and seen as the intensity differences in the image. Hence, the texture analysis may be based on detection of objects from the image data having a texture differing from a reference value. As a non-limiting example, the intensity differences are represented in the image data as the contrast. Moreover, the reference value may be determined in accordance with the food product under inspection. For example, it may be determined that if a food product complies with quality requirements all intensity difference values definable with a certain accuracy shall be below the reference value with a known imaging configuration. Correspondingly, the same applies with any other value or values selected to represent the texture. Now, if during the texture analysis it is detected, based on information derivable from intensity differences in the image, that a number of portions of the image data comprise texture values exceeding the corresponding reference value(s), it may be concluded that the quality requirements are not complied with and a generation a first set of detections may be initiated. The generation of the first set of detections may refer to a generation of a data record comprising data identifying each detection in a predetermined manner. The identification of the detection may e.g. comprise, but is not limited to, expressing a portion of the image data, e.g. as a position, which generated the detection, with any other data relating to the detection, such as value of the X-ray intensity. Naturally, such portion of the image data may be expressed as pixels or pixel areas or in any corresponding manner allowing the identification of the portions of the image data.

Moreover, in various embodiments the texture analysis 220 may comprise a further step in which a likelihood of correctness of a detection is determined. The likelihood may be calculated by applying one or more rules to the detections belonging to the first set. The number of rules may e.g. comprise of size, shape or intensity difference. In response to the determination of the likelihoods of the detection a sub-set of detections from the first set may be established. The sub-set may e.g. be defined to comprise detection having a likelihood within some predetermined range.

According to various embodiments a pattern analysis may also be performed 230 to at least part of the image data. An aim of the pattern analysis is to identify objects with predetermined pattern, like a shape, from the image data. In response to an identification of an object with a predetermined pattern from the image data a detection under pattern analysis may be performed. A second set of detections may be generated, the second set of detections comprising data identifying detections performed under the pattern analysis. As indicated e.g. in the FIG. 2 the pattern analysis 230 may be performed at least partly concurrently to the texture analysis 220. However, it is also possible to arrange that they are performed consequently to each other.

In accordance with various embodiments the pattern analysis 230 may be performed with a machine-learning component. The machine-learning component refers to a neural network model trained with a training data to perform the pattern analysis to the image data in the food inspection device. Depending on a task to which the machine-learning component is trained to the training data may be selected in accordance with the application environment of the food inspection machine. In other words, the training data may e.g. comprise typical patterns belonging to the food product itself, but also patterns derivable from a food product manufacturing process, such as patterns of parts belonging to devices in the manufacturing chain, for example. A more detailed description of an applicable pattern recognition process with a machine learning component is given in a forthcoming description.

As mentioned above in some embodiments the pattern analysis may be performed to the image data as a whole. On the other hand, in some embodiments the pattern analysis may be performed only to detections disclosed in the first set of detections originating from the texture analysis. Alternatively, in some further embodiments the pattern analysis may be performed to the sub-set of the first set of detections defined on a basis of a likelihood of correctness of the detections in the texture analysis. In the latter embodiments an outcome of the pattern analysis may e.g. be if the detection performed with the texture analysis is correct or incorrect, for instance. In at least some these kinds of arrangements the texture analysis 220 shall be performed at least in part prior to the pattern analysis 230 to enable a consecutive analysis as disclosed.

In response to a generation of detection results from the texture analysis 220 and the pattern analysis 230 a combined result is to be generated (cf. step 240 in FIG. 2). An aim is to generate an indication 250 of the inspection of the food product on a basis of the generated first set of detections and the second set of detections which are combined in step 240. Thus, the indication may be based on detections from both the first set of detections and the second set of detections, or in accordance with any combination of the these two. In various embodiments the combining 240 may be established so that the texture analysis is arranged to generate detections on objects having a size within a first range and the pattern analysis is arranged to generate indications on objects having a size within a second range being at least in part smaller than the first range. For example, if either one of the analysis generates a detection, the combined result of the analysis is that the food product under monitoring deviates from expected, and an indication is to be generated 250. In some other embodiments of the invention the combined result causing the generation of the indication 250 may be defined so that the indication is generated only on a condition that both the texture analysis and the pattern analysis generate a detection on a basis of the same portion of the image. Still further, in some embodiments a likelihood of the detection (s) may be taken into account in a decision-making if the indication is to be generated or not 250.

The indication itself may be output with any applicable I/O device 120, such as by generating visual and/or audio notification on the outcome of the inspection as the indication. For example, the outcome may express if the food product complies with quality standards set for the food product or not.

For sake of clarity and as mentioned in the foregoing description the texture analysis and the pattern analysis may be executed concurrently at least in part or consecutively to each other.

Figure 3:
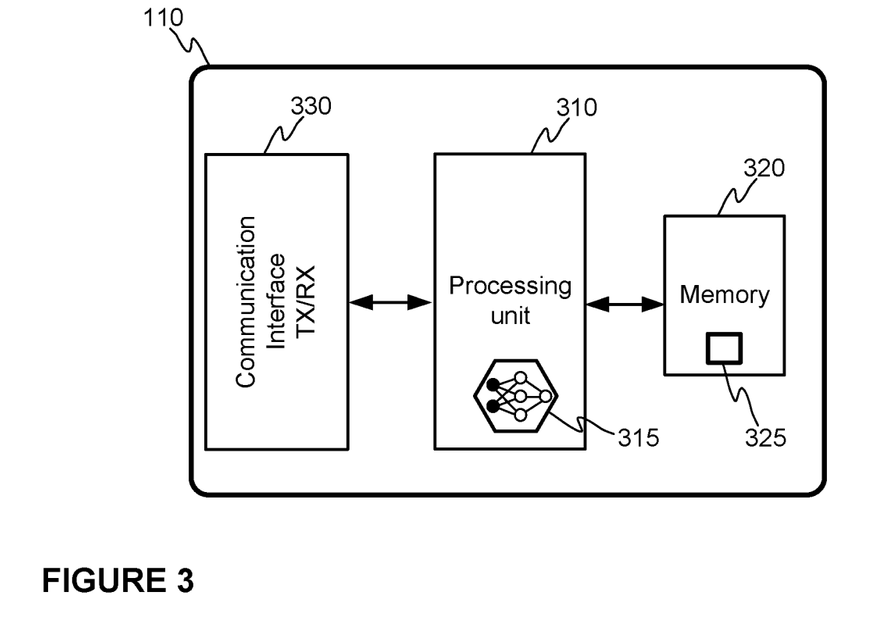
FIG. 3 illustrates schematically a control unit according to an embodiment of the invention.

The above described method may be executed by the control unit 110 of the food inspection device. FIG. 3 illustrates schematically a non-limiting example of the control unit 110 as a block diagram. Several functionalities may be carried out with a single physical device, e.g. all calculation procedures may be performed in a single processor if desired. The control unit 110 according to an example of FIG. 3 comprises a main processing unit 310, a memory 320 storing at least a computer program code 325 and a communication interface 330. The control unit 110 may further comprise, or have access to, a storage device, an input/output device(s). The entities belonging to the control unit 110 may be connected to each other via a data bus, for example. The main processing unit 310 is a processing unit comprising processor circuitry and arranged to process data within the data processing system. The memory 320 and the communication interface 330 as well as the other entities may include conventional components as recognized by those skilled in the art. The memory 320 and storage device may store data within the control unit 110. As said computer program code 325 may reside in the memory 320 for implementing, for example, the method as described. Accordingly, a skilled person readily recognizes that an apparatus operating as the control unit 110 may be any data processing device, such as a computer device, a personal computer, a server computer, a mobile phone, a smart phone or an Internet access device, for example Internet tablet computer.

It is worthwhile to understand that different embodiments allow different parts to be carried out in different elements. For example, various processes of the food inspection device may be carried out in one or more processing devices; for example, entirely in one computer device, or in one server device or across multiple devices. The elements of executed process may be implemented as a software component residing on one device or distributed across several devices, as mentioned above, for example so that the devices form a so-called cloud.

In FIG. 3 it is schematically illustrated a machine-learning component 315 executable with the main processing unit 310 or with a dedicated processing unit. The machine-learning component 315 is dedicated at least to perform a pattern analysis as described in at least some example embodiments of the invention. In other words, the operation of the pattern analysis may be based on so-called deep learning. Deep learning may be considered as a sub-field of machine learning. Deep learning may involve learning of multiple layers of nonlinear processing units, either in supervised or in unsupervised manner. These layers form a hierarchy of layers, which may be referred to as artificial neural network. Each learned layer extracts feature representations from the input data, where features from lower layers represent low-level semantics (i.e. more abstract concepts). Unsupervised learning applications may include pattern analysis (e.g. clustering, feature extraction) whereas supervised learning applications may include classification of image objects in the task of the pattern analysis.

Generally speaking, deep learning techniques allow for recognizing and detecting objects in images with great accuracy, outperforming previous methods. One difference of deep learning image recognition, or analysis, technique compared to previous methods is learning to recognize image objects directly from the raw image data, whereas previous techniques are based on recognizing the image objects from hand-engineered features (e.g. SIFT features). During the training stage, deep learning techniques build hierarchical layers which extract features of increasingly abstract level.

Figure 4:
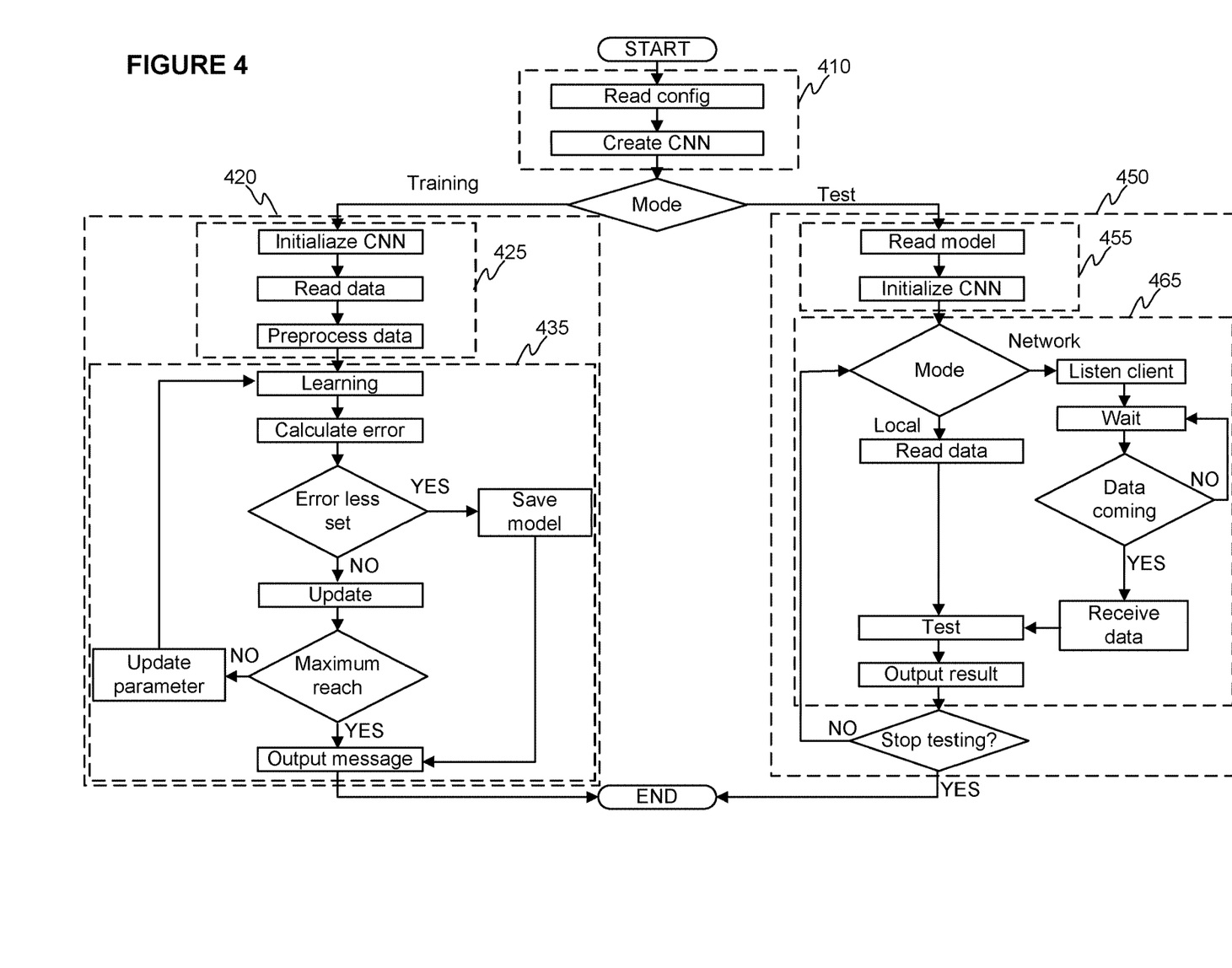
FIG. 4 illustrates schematically aspects relating to a neural network implementing at least a part of a method according to an embodiment of the present invention.

In order to achieve the neural network to perform a pattern analysis for the task of food inspection, it needs to be prepared for the task. FIG. 4 illustrates schematically aspects relating to a neural network arranged to perform a pattern analysis at least in part. The neural network may e.g. be a Convolutional Neural Network (CNN) for a purpose of the present invention. More specifically, FIG. 4 illustrates schematically aspects relating to a training of the neural network as well as aspects of testing the CNN. As a preliminary requirement is to set up 410 a convolutional network to be trained. This may be achieved by reading input configuration data based on which the CNN may be created. Now, it may be inquired from a user of a computing device implementing a process of FIG. 4 if a task is to train the CNN or to test an existing CNN. The training procedure is referred with 420 in FIG. 4 whereas the testing procedure is referred with 450. The training procedure 420 may comprise operations forming the training procedure 420. The operations may be organized to cover a preparation phase 425 and a training phase 435. In the preparation phase 425 a training data may be read to a memory and it may be preprocessed if needed. In the training phase 435 the CNN is trained with the training data by monitoring an error between an output received with known input and known output. If the error is less than defined, the CNN model may be saved. If the error is more than allowed, the training may be continued by updating parameters of the CNN. However, a maximum number of iterative rounds to the training may be set and if that is reached, the training phase may also be discontinued. In the described manner the training of the CNN may be achieved.

Correspondingly, the generated Convolutional Neural Network may be tested with the testing procedure 450. The testing procedure 450 may also comprise several operations which may e.g. be a preparation phase 455 and a testing phase 465. In the preparation phase 455 the CNN is initialized. According to an example embodiment it may e.g. be inquired from a user if the testing process is intended to be performed locally in a computing device or in a communication network together with a client device. In both cases the data received from the test process may be input to the CNN and the CNN is arranged to generate an output in the testing phase 465. On the basis of the testing result it may be decided if there is need to continue the testing procedure 450 or not.

Figure 5:
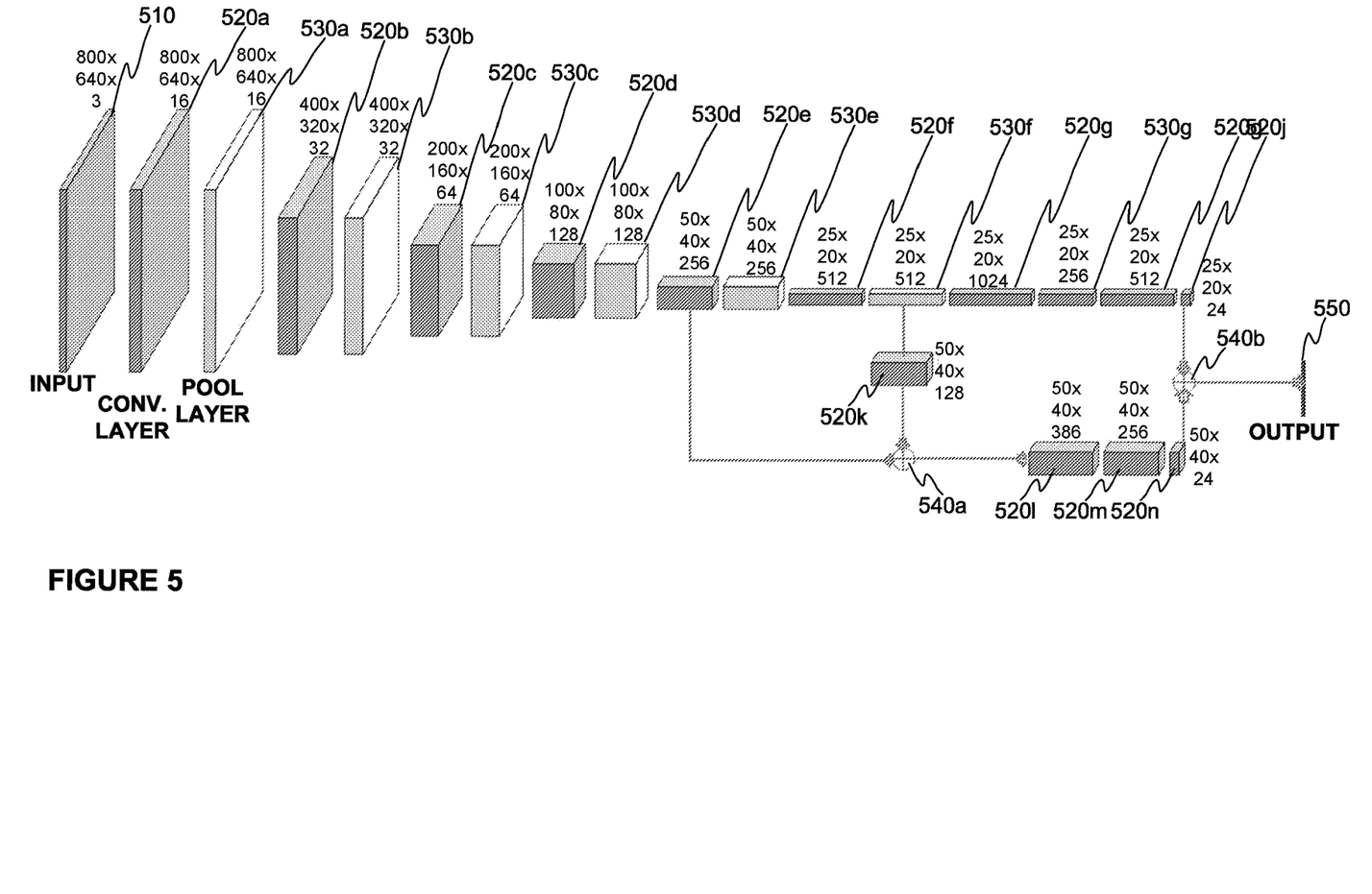
FIG. 5 illustrates schematically further aspects of the neural network according to an embodiment of the present invention.

FIG. 5 illustrates schematically a high-level example of a Convolutional Neural Network applicable for the task to perform pattern analysis 230. The Convolutional Neural Network receives X-ray image data as an input 510, and the convolutional layers (referred with 520a-520n in FIG. 5) perform convolution operations on the image data with weights shared spatially. Pool layers, or pooling layers (referred with 530a-530f in FIG. 5), in turn, are responsible for reducing a spatial size of the convolved feature. The sizes of the matrices in the convolutional layers 520a-520n and in the pool layers 530a-530f are adjusted in accordance with the application area in order to have an output with a desired accuracy. In FIG. 5, some non-limiting examples of the sizes of the matrices are given in a context of respective layers. The Convolutional Neural Network applicable to the task according to example embodiments may also comprise a first summing function 540a, or called as a first fusion function, and a second summing function 540b or called as a fusion second function. This purpose of the first summing function 540a is to combine the output convolutional features of 520e and 530f (where the features scale of 530f are set to be the same as 520e by module 520k). The main purpose of this operation is to generate a new route of the feature description for the target object. Moreover, the second summing function 540b performs the summing function for conducting a fusion operation of the likelihood probabilities, which are generated from the outputs of 520j and 520n, which are the full-connected layers of two routes, respectively. The main purpose is to obtain a joint probability for the final decision of detection. As a result, i.e. as an output 550, the CNN generates detection result in accordance with the present invention based on the pattern recognition.

The advantage of applying neural networks in the application area of food inspection comes from the internal representation which is built inside the layers. This representation is distributed among many units and is hierarchical, where complex concepts build on top of simpler concepts. As discussed in the foregoing description with respect to FIG. 4, the neural network has two main modes of operation: learning (a.k.a. training) phase and testing phase. The learning phase is the development phase, where the network is learnt to perform the final task. Learning may involve iteratively updating the weights or connections between units. The testing phase is the phase in which the network actually performs the task. Learning may be performed in several ways, for example, as a supervised learning, as unsupervised learning, or a reinforcement learning. In supervised learning, the network is provided with input-output pairs, where the output is usually a label. In supervised learning, the network is provided only with input data (and also with output raw data in case of self-supervised training). In reinforcement training, the supervision is sparser and less precise; instead of input-output pairs, the network gets input data and, sometimes, delayed rewards in the form of scores (e.g., −1, 0, or +1).

The invention as described by providing aspects with various embodiments may be applied to various tasks in the food product inspection area. For example, by means of the described elements it may be arranged that only those detections which are detected with a predetermined likelihood (e.g. 100%) are taken into account from the texture analysis. The rest of the detections may be performed with the pattern analysis by applying the machine-learning component to at least part of the image data. This implementation may operate so that the texture analysis reveals items having a size exceeding a predetermined limit whereas pattern analysis reveals items having the smaller size. For achieving this, the training of the machine-learning component may be arranged with training data defining objects having the smaller size than detectable with the texture analysis.

Moreover, the solution according to the invention allows to perform the food product inspection with food products in which there may be objects, such as an object belonging to the food product and another object being a foreign object, having intensity difference close to each other. In such a situation the texture analysis may not generate a detection since it is challenging, or even impossible, to distinguish the objects based on the intensity differences, but the pattern analysis may generate a detection e.g. of the foreign object. For example, a wish bone ended up to the chicken food product, such as to a package, may be identified based on a known shape of the wish bone.

Still further, the inspection method according to the invention may be applied in confirming that a detection made with the texture analysis is correct. For example, the food product may include an item which is detected with the texture analysis. Due to the detection performed with the texture analysis it may be considered that there is a foreign object in the food product. In response to a detection with the texture analysis it may be arranged that the pattern analysis is directed at least to the portion of the image data, which generated the detection in the texture analysis, to confirm that the detection is correct. For example, the machine-learning component may be trained to identify items belonging to the food product, and by applying that knowledge, the pattern analysis may generate an analysis result, that the detected object with the texture analysis actually belongs to the food product, in cancel on that basis the detection with the texture analysis. Naturally, a rule may be set for the pattern analysis that certain pattern, i.e. item, shall be found from the food product, or otherwise an indication indicating a "false" product may be generated.

The above given use cases are non-limiting examples of application possibilities of the present invention, and further use cases may be introduced.

As becomes clear from the foregoing description at least one aim of the present invention is to detect objects, especially contaminants or foreign objects, from a food product represented by an X-ray image. In accordance with the present invention a novel fusion approach by ensembling, or combining, two strategies based on low-level and high-level feature extraction and visual understanding. The low-level analysis may be based on so-called image background modeling to deal with the middle-to-small scale inspection, while so-called high-level analysis may be based on the image foreground modeling to handle the small-to-tiny scale challenges in object detection. For sake of clarity, the expression "image background" may be considered to refer to areas occupied by the inspected food product in the generated X-ray image. Moreover, the expression "image foreground" may be considered to refer to areas occupied by the contaminants/foreign objects in the generated X-ray image or the areas occupied by the elements for quality parameters being analyzed.

In order to implement the above-described approach an intelligent comprehensive food product inspection apparatus for food production is developed including X-ray imaging devices, machine vision software and integrated automatic electrical control system. In the solution a machine-learning strategy is introduce in which different kernelized texture feature descriptors are used to localize the abnormal intensity/gradient changes in the X-ray image and redesigning an improved deep neuron network structure to achieve accurate and robust inspections in the images containing more challenging textures and intensity variations not being able to be managed by a texture analysis.

The specific examples provided in the description given above should not be construed as limiting the applicability and/or the interpretation of the appended claims. Lists and groups of examples provided in the description given above are not exhaustive unless otherwise explicitly stated.

What is claimed is:
1. A method for inspecting a food product, the method comprising:
  receiving image data representing the food product captured with an X-ray imaging unit;
  performing a texture analysis to the received image data to generate a first set of detections;
  performing a pattern analysis to at least part of the image data, the pattern analysis being performed with a machine-learning component trained to identify objects with predefined pattern, to generate a second set of detections; and
  generating an indication of an outcome of an inspection of the food product in accordance with a combination of the generated first set of detections and the second set of detections by detecting with the texture analysis objects having a size within a first range and detecting with the pattern analysis objects having a size within a second range being at least in part smaller than the first range.

2. The method of claim 1, wherein the texture analysis comprises generating a sub-set of the first set of detections, the sub-set comprising detections having a likelihood within a predetermined range.

3. The method of claim 2, wherein the at least part of the image data to which the pattern analysis is performed corresponds to the sub-set of the first set of detections.

4. The method of claim 3, wherein an outcome of the pattern analysis performed to the sub-set of the first set of detections is one of: the detection performed with the texture analysis is correct, and the detection performed with the texture analysis is incorrect.

5. The method of claim 4, wherein the machine-learning component is trained with object data derivable from a process by which the food product is manufactured.

6. The method of claim 3, wherein the machine-learning component is trained with object data derivable from a process by which the food product is manufactured.

7. The method of claim 2, wherein the machine-learning component is trained with object data derivable from a process by which the food product is manufactured.

8. The method of claim 1, wherein the machine-learning component is trained with object data derivable from a process by which the food product is manufactured.

9. An apparatus for inspecting a food product, the apparatus comprising:
an X-ray imaging system configured to generate image data representing the food product; and
a controller configured to:
receive the image data representing the food product captured with the X-ray imaging system,
perform a texture analysis to the image data to generate a first set of detections,
perform a pattern analysis to at least part of the image data, the pattern analysis being performed with a machine-learning component trained to identify objects with predefined pattern, to generate a second set of detections, and
generate an indication of an outcome of an inspection of the food product in accordance with a combination of the generated first set of detections and the second set of detections by detecting with the texture analysis objects having a size within a first range and detecting with the pattern analysis objects having a size within a second range being at least in part smaller than the first range.

10. The apparatus of claim 9, wherein the controller is configured to, in the texture analysis, generate a sub-set of the first set of detections, the sub-set comprising detections having a likelihood within a predetermined range.

11. The apparatus of claim 10, wherein the controller is configured to perform the pattern analysis to the at least part of the image data corresponding to the sub-set of the first set of detections.

12. The apparatus of claim 11, wherein the controller is configured to generate, as an outcome of the pattern analysis performed to the sub-set of the first set of detections, one of: the detection performed with the texture analysis is correct, and the detection performed with the texture analysis is incorrect.

13. The apparatus of claim 9, wherein the machine-learning component of the controller unit is configured to be trained with object data derivable from a process by means of which the food product is manufactured.

14. A computer program product comprising at least one non-transitory computer-readable storage medium having computer-executable program code instructions stored therein, the program code instructions being configured, when the computer program product is executed on a computer, to cause the computer to at least:
receive the image data representing the food product captured with an X-ray imaging system;
perform a texture analysis to the image data to generate a first set of detections;
perform a pattern analysis to at least part of the image data, the pattern analysis being performed with a machine-learning component trained to identify objects with predefined pattern, to generate a second set of detections; and
generate an indication of an outcome of an inspection of the food product in accordance with a combination of the generated first set of detections and the second set of detections by detecting with the texture analysis objects having a size within a first range and detecting with the pattern analysis objects having a size within a second range being at least in part smaller than the first range.

* * * * *